(12) United States Patent
Kinet et al.

(10) Patent No.: US 7,811,568 B2
(45) Date of Patent: Oct. 12, 2010

(54) SMALLPOX MONOCLONAL ANTIBODY

(75) Inventors: Jean-Pierre Kinet, Lexington, MA (US); Marie-Helene Jouvin, Jamaica Plain, MA (US)

(73) Assignee: Quercegen Pharma, Newton, MA (US)

( * ) Notice: Subject to any disclaimer, the term of this patent is extended or adjusted under 35 U.S.C. 154(b) by 294 days.

(21) Appl. No.: 11/843,415

(22) Filed: Aug. 22, 2007

(65) Prior Publication Data

US 2008/0112959 A1 May 15, 2008

Related U.S. Application Data

(60) Provisional application No. 60/839,579, filed on Aug. 23, 2006.

(51) Int. Cl.
*A61K 31/42* (2006.01)
(52) U.S. Cl. ............... 424/147.1; 530/350; 530/387.1; 530/387.3; 530/388.1; 530/388.3; 530/387.9; 424/133.1; 424/159.1; 424/139.1; 536/23.5; 435/69.1; 435/320.1; 435/325; 435/339; 435/331
(58) Field of Classification Search ........... 530/350, 530/387.1, 387.3, 388.1, 388.3, 387.9; 424/133.1, 424/139.1, 147.1, 159.1; 435/69.1, 320.1, 435/325, 331, 339; 536/23.5
See application file for complete search history.

(56) References Cited

U.S. PATENT DOCUMENTS

| | | | |
|---|---|---|---|
| 6,451,309 | B2 | 9/2002 | Hooper et al. |
| 6,620,412 | B2 | 9/2003 | Hooper et al. |
| 2002/0009447 | A1 | 1/2002 | Hooper et al. |
| 2003/0022226 | A1 | 1/2003 | Hooper et al. |

OTHER PUBLICATIONS

Greenspan et al. (Nature Biotechnology. 1999; 7: 936-937).*
Mariuzza et al. (Annu. Rev. Biophys. Biophys. Chem. 1987; 16: 139-159).*
Gussow et al. (Methods in Enzymology. 1991; 203: 99-121).*
Giusti et al. (Proc. Natl. Acad. Sci. USA. May 1987; 84 (9): 2926-2930).*
Chien et al. (Proc. Natl. Acad. Sci. USA. Jul. 1989; 86 (14): 5532-5536).*
Caldas et al. (Mol. Immunol. May 2003; 39 (15): 941-952).*
Lustig et al., "Combinations of Polyclonal or Monoclonal Antibodies to Proteins of the Outer Membranes of the Two Infectious Forms of Vaccinia Virus Protect Mice against a Lethal Respiratory Challenge," Journal of Virology, 79(21):13454-13462 (2005).
Ramirez et al., "Administration to Mice of a Monoclonal Antibody that Neutralizes the Intracellular Mature Virus Form of Vaccinia Virus Limits Virus Replication Efficiently under Prophylactic and Therapeutic Conditions," Journal of General Virology, 83:1059-1067 (2002).
Schmelz et al., "Assembly of Vaccinia Virus: The Second Wrapping Cisterna Is Derived from the Trans Golgi Network," Journal of Virology, 68(1):130-147 (1994).
Bell et al., "Antibodies against the Extracellular Enveloped Virus B5R Protein are Mainly Responsible for the EEV Neutralizing Capacity of Vaccinia Immune Globulin," *Virology*. 01 vol. 325, No. 2, pp. 425-431; see entire document (e.g., the abstract), 2004.
Sawyer et al., "Antibodies for the Prevention and Treatment of Viral Diseases," *Antiviral Res*. vol. 47, No. 2, pp. 57-77, see entire document (e.g., the abstract), 2000.

\* cited by examiner

*Primary Examiner*—Stephen L Rawlings
(74) *Attorney, Agent, or Firm*—Occhiuti Rohlicek & Tsao LLP

(57) ABSTRACT

Humanized monoclonal antibodies against the vaccinia virus B5R surface antigen. The antibodies are effective in treating smallpox infection. Also disclosed are nucleic acids that encode the heavy and light chains of such antibodies and cells that express them.

11 Claims, No Drawings

SMALLPOX MONOCLONAL ANTIBODY

RELATED APPLICATION

This application claims priority to U.S. Provisional Application Ser. No. 60/839,579, filed on Aug. 23, 2006, the contents of which are incorporated by reference in its entirety.

BACKGROUND

Smallpox is a serious, highly contagious, and sometimes fatal infectious disease caused by the variola virus, a member of the poxvirus family. Smallpox outbreaks have occurred from time to time for thousands of years, but the disease was effectively eradicated by 1977 after a successful worldwide vaccination program. After this disease was eliminated, routine vaccination against smallpox among the general public was stopped because it was no longer necessary for prevention. Consequently, a large fraction of the current human population has not been immunized against smallpox. As a result, a bioterrorist variola virus attack would be devastating. Importantly, were such an attack carried out, vaccination would be too slow to effectively arrest the rapid spread of smallpox in the targeted population. There is therefore a need for rapidly acting and effective compositions for treating smallpox infection.

SUMMARY

The present invention is based, in part, on the unexpected finding that a humanized monoclonal antibody against the B5R antigen of vaccinia virus, a member of the poxvirus family closely related to variola virus, is effective for neutralizing a smallpox infection.

Accordingly, one aspect of the invention relates to a humanized monoclonal antibody containing antigen-binding domains directed against a B5R antigen. Such a humanized monoclonal antibody (hB5RmAb) can slow progression of a vaccinia virus infection when administered to a subject suffering from a vaccinia virus infection. It can have the same epitope specificity as the monoclonal antibody produced by the EM-1000 hybridoma cell line (ATCC Deposit Designation PTA-7594). The humanized antibody can include a first heavy chain complementarity determining region (CDR) sequence identical to SEQ ID NO:1 (shown below) with up to two single amino acid differences, a second heavy chain CDR sequence identical to SEQ ID NO:2 (shown below) with up to four single amino acid differences, and a third heavy chain CDR sequence identical to SEQ ID NO:3 (shown below) with up to four single amino acid differences; and a first light chain CDR sequence identical to SEQ ID NO:4 (shown below) with up to four single amino acid differences, a second light chain CDR sequence identical to SEQ ID NO:5 (shown below) with up to three single amino acid differences, and a third light chain CDR sequence identical to SEQ ID NO:6 (shown below) with up to three single amino acid differences. The humanized antibody can consist of a single polypeptide containing the above-described heavy chain and light CDR sequences.

Another aspect of the invention relates to a cultured cell that contains the above-described antibody.

A further aspect of the invention relates to an isolated nucleic acid encoding a polypeptide that contains a humanized heavy chain variable region sequence containing the above-described heavy chain or light chain CDR sequences.

Yet another aspect of the invention relates to a cultured cell containing one of the just-described nucleic acids.

Other features or advantages of the present invention will be apparent from the following detailed description, and also from the claims.

DETAILED DESCRIPTION

Described below are novel humanized monoclonal antibodies derived from donor (e.g., rat or mouse) monoclonal antibodies against vaccinia virus B5R antigen (hB5RmAb) that are useful for both detecting variola virus and inhibiting its ability to infect host cells. Administration of rodent mAbs as therapeutic agents in humans can give rise to a potentially hazardous immune response. The humanized monoclonal antibodies of the present invention do not trigger this immune response and thus can be used as therapeutic or prophylactic agents.

As used herein, the term "monoclonal antibody," refers to any polypeptide containing an immunoglobulin heavy chain or light chain variable region. Such polypeptides include, e.g., divalent antibodies, monovalent antibodies, single chain antibodies (i.e., a single polypeptide containing heavy chain and light chain variable regions), Fab fragments, diabodies, minibodies, and fusions thereof to an amino acid sequence unrelated or of low (i.e., less than 60%) sequence identity to that of any immunoglobulin.

The term "humanized monoclonal antibody" refers to any of the foregoing polypeptides in which at least one of the variable region framework sequences is close or identical to a human framework sequence, e.g., an antibody isolated from a human immunoglobulin phage display library.

The sequence of the B5R protein (GENBANK CAA46496) recognized by the hB5RmAbs described herein is shown below:

```
                                              (SEQ ID NO: 7)
MKTISVVTLLCVLPAVVYSTCTVPTMNNAKLTSTETSFNDKQKVTFTCDS

GYYSLDPNAVCETDKWKYENPCKKMCTVSDYVSELYNKPLYEVNAIITLI

CKDETKYFRCEEKNGNTSWNDTVTCPNAECQSLQLDHGSCQPVKEKYSFG

EHITINCDVGYEVIGASYITCTANSWNVIPSCQQKCDIPSLSNGLISGST

FSIGGVIHLSCKSGFILTGSPSSTCIDGKWNPVLPICIRSNEEFDPVEDG

PDDETDLSKLSKDVVQYEQEIESLEATYHI IIVALTIMGVIFLISVIVL

VCSCNKNNDQYKFHKLLL
```

Assays that can be used for determining the affinity of the parental or humanized antibody for the B5R antigen are well known in the art. See, e.g., Azimzadeh et al., J. Immunol Methods, 141(2):199-208 (1991); and Ota et al., Hybridoma, 17(5):471-7 (1998). hB5RmAbs can have the same B5R antigen epitope specificity as the antibody produced by the EM-1000 hybridoma (described below). Methods for epitope mapping are well established and can be readily carried out as illustrated in, e.g., Steinmann et al., J Virol. 78(17):9030-40 (2004).

The hB5RmAbs described herein can have the following first, second, and third heavy chain complementarity determining regions (H-CDRs 1-3), derived from a donor (e.g., mouse or rat) monoclonal antibody against a B5R antigen:

| H-CDR 1 | NYHVH | (SEQ ID NO: 1) |
| H-CDR 2 | LMWRDGDTSYNPTLKS | (SEQ ID NO: 2) |

```
                    -continued
H-CDR 3      GSEYYGLLGYVMGA        (SEQ ID NO: 3)
```

They can have the following first, second, and third light chain complementarity determining regions (L-CDRs 1-3):

```
L-CDR 1      KASKSISKSLA           (SEQ ID NO: 4)

L-CDR 2      SGSTLQS               (SEQ ID NO: 5)

L-CDR 3      QQHNEYPVT             (SEQ ID NO: 6)
```

As pointed out in the Summary section above, each of the CDR sequences in the hB5RmAbs described herein can include a number of amino acid differences with respect to the above listed SEQ ID NOs: 1-6:

| H-CDR 1 | up to 2 single amino acid differences compared to SEQ ID NO: 1 |
| H-CDR 2 | up to 4 single amino acid differences compared to SEQ ID NO: 2 |
| H-CDR 3 | up to 4 single amino acid differences compared to SEQ ID NO: 3 |
| L-CDR 1 | up to four single amino acid differences compared to SEQ ID NO: 4 |
| L-CDR 2 | up to three single amino acid differences compared to SEQ ID NO: 5 |
| L-CDR 3 | up to three single amino acid differences compared to SEQ ID NO: 6. |

Differences can include amino acid substitutions, deletions, insertions, and additions. Where the difference is an amino acid substitution, conservative amino acid substitutions are preferable. A conservative amino acid substitution is one in which one amino acid is substituted by another amino acid having similar chemical properties. Table 1 illustrates how the 20 genetically encoded amino acids can be grouped according to their chemical properties.

TABLE 1

Amino Acids Grouped According to Chemical Properties

| Acidic | Neutral | Aliphatic | Aromatic | Basic |
|---|---|---|---|---|
| Aspartate, Glutamate | Asparagine, Cysteine Glutamine, Methionine, Proline, Serine, Threonine | Alanine, Glycine, Isoleucine, Leucine, Valine | Histidine, Phenylalanine, Tryptophan, Tyrosine | Arginine, Lysine |

Techniques for introducing any of the foregoing mutations are well known in the art (e.g., site-directed mutagenesis, error-prone PCR, and sequence replication in an error-prone host cell). The ability of hB5RmAbs containing any of the above-described types of mutations to bind to B5R can be tested very efficiently by a number of commonly used techniques, e.g., by ELISA or phage display. High-throughput versions of these assays are known in the art and can be used in combination with mutagenesis techniques to isolate hB5RmAbs having even higher antigen affinity without undue effort. See, e.g., U.S. Pat. No. 6,916,474.

For the variable region of a hB5RmAb, any human acceptor variable region framework sequence may be used having regard to class or type of the donor antibody from which the antigen binding regions are derived. The human acceptor variable region framework sequence can also be a consensus sequence, i.e., one that is generated based on several naturally occurring sequences. It is preferred that the type of human acceptor framework used be of the same or similar class or type as that of the donor antibody. Preferably, the human group III gamma germ line frameworks are used for the composite heavy chain and the human group I kappa germ line frameworks are used for the composite light chains. The heavy and light chains of hB5RmAbs can each include up to about 15 residues from a donor variable region framework sequence. Including donor variable region framework residues within hB5RmAb framework region sequences can augment the affinity of the antibody for its antigen. Methods for selecting suitable donor framework residues are described, e.g., in U.S. Pat. Nos. 5,998,586 and 6,056,957.

The constant region domains of the hB5RmAbs described herein are selected having regard to the proposed functions of the antibody, in particular, the effector functions, which may be required. For example, the constant region domains may be human IgA, IgE, IgG or IgM domains. In particular, IgG human constant region domains may be used, especially of the IgG1 and the IgG3 isotype, when the hB5RmAb is intended for therapeutic uses and antibody effector functions are required. Modified human constant region domains may also be used in which one or more amino acid residues have been altered or deleted to change a particular effector function.

The hB5RmAbs described herein can have attached effector or reporter molecules (e.g., as fusion polypeptides). Alternatively, the amino acid sequence of the constant region of a heavy chain or light chain can be replaced with the amino acid sequence encoding a functional non-immunoglobulin polypeptide, e.g., an affinity tag, a fluorescent protein, an enzyme, or a toxin molecule. Thus, the remainder of the antibody molecules need not comprise only sequences from immunoglobulins.

Further aspects of the invention include DNA sequences coding for the humanized heavy and light chains that form a hB5RmAb. The cloning and expression vectors containing the DNA sequences, host cells transformed with the DNA sequences and the processes for producing the antibody molecules comprising expressing the DNA sequences in the transformed host cells are also further aspects of the invention. The general methods by which vectors may be constructed, transfection methods and culture methods are well known in the art and are readily carried out without undue effort. The DNA sequences which encode the anti-B5R donor amino acid sequences may be readily obtained by well known methods, as illustrated in, e.g., International Patent Application No. WO 93/16184). For example, the anti-B5R coding sequences may be obtained by genomic cloning or cDNA cloning from suitable hybridoma cell lines. Positive clones may be screened using appropriate probes for the heavy and light chains required. Alternatively, PCR cloning may be used.

Human acceptor amino acid sequences may be obtained by any of a number of standard methods. For example, DNA sequences coding for human acceptor frameworks, such as human group I light chains and human group III heavy chains, are known and widely available to workers in the art.

Standard molecular biology techniques may be used to prepare the desired DNA sequences. The sequences may be synthesized completely or in past using oligonucleotide synthesis techniques. Site-directed mutagenesis and PCR techniques may be used as appropriate. For example, oligonucleotide directed synthesis as described by Jones et al. *Nature,* 321, 522 (1986) can be used. Oligonucleotide directed mutagenesis of a pre-existing variable region as described by Verhoeyen et al. *Science,* 239, 1534-1536 (1988) can also be used. Further, enzymatic filling-in of gapped oligonucleotides using T4 DNA polymerase as described in Queen et al, *Proc. Natl. Acad. Sci. USA*, 86, 10029-10033 (1989) and WO 90/0786.1) may be use.

Nucleic acids can also be custom ordered from a variety of commercial sources, such as SIGMA-GENOSYS (at sigma-genosys.com/oligo.asp); The Midland Certified Reagent Company (mcrc@oligos.com), The Great American Gene Company (at genco.com), EXPRESSGEN Inc. (at expressgen.com), Operon Technologies Inc. (Alameda, Calif.), and many others.

Any suitable host cell and vector system may be used for the expression of DNA sequences encoding a hB5RmAb heavy or light chain. Preferably, eukaryotic (e.g. mammalian) host cell expression systems are used. In particular, suitable mammalian host cells include CHO cells and myeloma or hybridoma cell lines.

In one embodiment, the hB5RmAb is secreted by the hybridoma line EM-1000. Applicants have deposited the EM-1000 hybridoma cell line (ATCC Deposit Designation PTA-7594), in compliance with the Budapest Treaty, with the American Type Culture Collection (ATCC) Manassas, Va. 20110-2209, U.S.A. The hybridoma line deposited was taken from the same deposit maintained by EMAB LLC, 3 Hunt Road, Lexington, Mass. 02421, since prior to the filing date of this application. The deposit of the hybridoma will be maintained without restriction in the ATCC depository for a period of 30 years, or 5 years after the most recent request, or for the effective life of the patent, whichever is longer, and will be replaced if the deposit becomes non-viable during that period.

The above-described hB5RmAbs can be incorporated into pharmaceutical compositions for prophylactic or therapeutic use. For example, a pharmaceutical composition can include an effective amount of a hB5RmAb and a pharmaceutically acceptable carrier. Generally, the effective amount will, result in a circulating hB5RmAb concentration sufficient to quantitatively bind circulating variola or vaccinia virus, or slows the progression of the infection in an infected subject. Nonetheless, effective amounts will vary, as recognized by those skilled in the art, depending on the severity of the infection, the stage of intervention, the general health or age of the subject, previous treatments, route of administration, excipient usage, and the possibility of co-usage with other prophylactic or therapeutic treatment.

Also within the scope of this invention is a method for treating smallpox infection in a subject, by administering to a subject in need thereof an effective amount of the above-described antibody. Subjects to be treated can be identified as having, or being at risk for having a condition related to smallpox infection. The term "treating" refers to administration of a composition to a subject with the purpose to cure, alleviate, relieve, remedy, or ameliorate a disorder, the symptom of the disorder, the disease state secondary to the disorder, or the predisposition toward the disorder. An "effective amount" is an amount of the composition that is capable of producing a medically desirable result in a treated subject.

To practice the methods of the present invention, a hB5RmAb-containing composition can be administered systemically via a parenteral route. When administered, the therapeutic composition is preferably in the form of a pyrogen-free, parenterally acceptable aqueous solution. The preparation of such a parenterally acceptable protein solution, having due regard to pH, isotonicity, stability and the like, is within the skill of the art. Among the parenterally acceptable vehicles and solvents that can be employed are mannitol, water, Ringer's solution, and isotonic sodium chloride solution.

As needed, hB5RmAbs can be administered continuously over a period of time. Methods for continually infusing a composition and sustaining its systemic concentration over time are known in the art. For example, the compositions described herein can be released or delivered from an osmotic mini-pump or other time-release device. The release rate from an elementary osmotic mini-pump can be modulated with a microporous, fast-response gel disposed in the release orifice. An osmotic mini-pump is useful for controlling release of the composition over an extended period of time (e.g., from one hour to one week). Such mini pumps as well as other sustained release devices are available commercially from, e.g., DURECT corporation (Cupertino, Calif.). An active composition can also be administered in the form, of suppositories for rectal administration.

The following specific example is to be construed as merely illustrative, and not limitative of the remainder of the disclosure in any way whatsoever. Without former elaboration, it is believed that one skilled in the art can, based on the description herein, utilize the present invention to its fullest extent. All publications cited herein are hereby incorporated by reference in their entirety.

Neutralization of Vaccinia Virus in vivo by Anti-BR5 Monoclonal Antibody

The rat hybridoma anti-BR5 directed against the vaccinia virus viral envelope protein B5R was grown in DMEM (Schmelz et al., *J. Virol.*, 68(1):130-147 (1994); and Galmiche et al., *Virology*, 254(1):71-80 (1999). The monoclonal antibody was purified on protein G SEPHAROSE.

Six to eight week, old Balb/c mice (3 per group) were infected intranasally with $10^7$ plaque forming units of vaccinia virus. Five hours later, they were injected intraperitonally with either 10 or 30 µg of anti-BR5 monoclonal antibody or pre-immune rat IgG (PI). The weight of the mice was then monitored every other day for 12 days. Results were compared between anti-BR5 and PI animals at each dose by unpaired one-sided/test.

In control animals, a drop in weight was observed at day 2 and peaked at day 6, and the mice recovered at day 12. In anti-BR5 treated animals, a similar pattern was observed. However, the drop in weight at day 6 was significantly less in animals having received 30 µg of anti-BR5 ($p<0.001$ compared to the PI condition).

Humanization of Anti-BR5 Monoclonal Antibody

The cDNA for the variable regions of anti-BR5 light and heavy chains were amplified by PCR, and subcloned into pCRII (Invitrogen) for sequence determination. Nucleotide sequences were obtained from several independent clones. Identical cDNA sequences from independent clones were chosen to represent the light or heavy chain V region of anti-BR5 antibody.

CDR grafting was applied for the humanization of rat anti-BR5 antibody. To retain binding affinity and specificity, it was essential to conserve the V region conformation when grafting the CDRs onto the human framework. After amino acid sequences comparison, the framework region of human antibody IC4 was used as framework donor for the humanization of rat anti-BR5.

Four pairs of primers (each around 80 bases in length) were designed and synthesized to encode the protein sequences of the humanized anti-BR5 variable regions, including the signal peptides. The primers in each pair overlapped by around 20 nucleotides. The assembling and amplification of the genes were conducted in four steps: (1) the four pairs of complementary oligonucleotides were annealed and extended with Klenow fragment in 4 separate reactions; (2)

the resulting four dsDNA fragments were mixed pair wise, denatured, reannealed, and extended in two separate reactions; (3) the resulting two dsDNA fragments were mixed, denatured, reannealed, and extended to create the final full-length dsDNA; and (4) the resulting DNA was amplified by PCR with primers to introduce an XbaI site at both ends. The PCR fragment was then digested by XbaI and inserted into the respective XbaI-digested pVk and pVg4 vectors.

The specificity of humanized anti-BR5 was then tested as described below. Plasmids encoding humanized anti-BR5 heavy and light chains were co-transfected into COS-7 cells. The exhausted supernatants from cultured cells were then collected and purified. Humanized anti-BR5 was tested for its ability to interact with the extracellular domain of B5R expressed in COS-7 cells or *E. coli* by western blot analysis.

To develop stable cell lines that produce humanized anti-BR5, plasmids encoding humanized anti-BR5 heavy and light chains were co-transfected together into CHO/dhfr-cells using lipofectamine 2000 (INVITROGEN). Twenty-four hours after transfection, cells were plated into 96-well tissue culture plates with selection medium (20 nM methotrexate in alpha MEM). MTX-resistant clones were tested for human IgG production. Limiting dilution was applied to identify high-yield monoclonal cell lines.

OTHER EMBODIMENTS

All of the features disclosed in this specification may be combined in any combination. Each feature disclosed in tins specification may be replaced by an alternative feature serving the same, equivalent, or similar purpose.

From the above description, one skilled in the art can easily ascertain the essential characteristics of the present invention, and without departing from the spirit and scope thereof, can make various changes and modifications of the invention to adapt it to various usages and conditions. Thus, other embodiments are also contemplated.

What is claimed is:

1. A humanized monoclonal antibody comprising an antigen-binding domain directed against a B5R antigen comprising the amino acid sequence of SEQ ID NO: 7, wherein said antibody binds to the B5R antigen and wherein said antigen-binding domain comprises a heavy chain variable region comprising a first heavy chain CDR sequence identical to SEQ ID NO:1, a second heavy chain CDR sequence identical to SEQ ID NO:2, and a third heavy chain CDR sequence identical to SEQ ID NO:3 and a light chain variable region comprising a first light chain CDR sequence identical to SEQ ID NO:4, a second light chain CDR sequence identical to SEQ ID NO:5, and a third light chain CDR sequence identical to SEQ ID NO:6.

2. The monoclonal antibody of claim 1, wherein the antibody, when administered to a subject suffering from a vaccinia virus infection, slows progression of the infection.

3. The monoclonal antibody of claim 1, wherein the antibody consists of a single polypeptide.

4. The monoclonal antibody of claim 1, wherein the antibody is the monoclonal antibody produced by cell line ATCC Deposit Designation PTA-7594.

5. An isolated nucleic acid comprising a nucleic acid sequence encoding a polypeptide comprising a humanized immunoglobulin heavy chain variable region containing a first CDR sequence identical to SEQ ID NO:1, a second CDR sequence identical to SEQ ID NO:2, and a third CDR sequence identical to SEQ ID NO:3.

6. An isolated nucleic acid comprising a nucleic acid sequence encoding a polypeptide comprising a humanized immunoglobulin light chain variable region containing a first CDR sequence identical to SEQ ID NO:4, a second CDR sequence identical to SEQ ID NO:5, and a third CDR sequence identical to SEQ ID NO:6.

7. A cultured cell comprising a nucleic acid molecule comprising a nucleotide sequence encoding the monoclonal antibody of claim 1.

8. A cultured cell comprising the nucleic acid of claim 5.

9. A cultured cell comprising the nucleic acid of claim 6.

10. The cultured cell of claim 9, further comprising an isolated nucleic acid comprising a nucleic acid sequence encoding a polypeptide comprising a humanized immunoglobulin heavy chain variable region containing a first CDR sequence identical to SEQ ID NO:1, a second CDR sequence identical to SEQ ID NO:2, and a third CDR sequence identical to SEQ ID NO:3.

11. A method for treating smallpox infection in a subject, the method comprises administering to a subject in need thereof an effective amount of an antibody of claim 1 to treat the smallpox infection in the subject.

* * * * *